United States Patent [19]

Newman et al.

[11] Patent Number: 5,670,680

[45] Date of Patent: Sep. 23, 1997

[54] METHOD FOR PRODUCING OCTAHYDROFLUORENYL METAL COMPLEXES

[75] Inventors: Thomas H. Newman; Jerzy Klosin; Peter N. Nickias, all of Midland, Mich.

[73] Assignee: The Dow Chemical Company, Midland, Mich.

[21] Appl. No.: 638,256

[22] Filed: Apr. 26, 1996

[51] Int. Cl.$^6$ ................ C07F 17/00; C07F 7/28
[52] U.S. Cl. ................ 556/53; 556/20; 556/56; 502/103; 502/117; 526/160; 526/943
[58] Field of Search ................ 556/20, 53, 56; 526/160, 943; 502/103, 117

[56] References Cited

U.S. PATENT DOCUMENTS

| | | | |
|---|---|---|---|
| 4,675,416 | 6/1987 | Brownstein | 549/3 |
| 4,808,680 | 2/1989 | Schmidt et al. | 526/160 |
| 4,851,598 | 7/1989 | Rosenblum et al. | 585/25 |
| 5,021,599 | 6/1991 | Beer et al. | 556/138 |
| 5,045,517 | 9/1991 | Campbell, Jr. et al. | 502/103 |
| 5,064,802 | 11/1991 | Stevens et al. | 502/155 |
| 5,066,741 | 11/1991 | Campbell, Jr. | 526/171 |
| 5,196,490 | 3/1993 | Campbell, Jr. et al. | 526/160 |
| 5,206,197 | 4/1993 | Campbell, Jr. | 502/103 |
| 5,447,151 | 9/1995 | Bruna et al. | 128/203.15 |
| 5,484,862 | 1/1996 | Siddall et al. | 526/88 |
| 5,492,974 | 2/1996 | Peifer et al. | 525/274 |
| 5,492,975 | 2/1996 | Peifer et al. | 525/274 |
| 5,536,797 | 7/1996 | Nickias et al. | 526/170 |

FOREIGN PATENT DOCUMENTS

| | | |
|---|---|---|
| 0277003 | 8/1988 | European Pat. Off. . |
| 0520732 | 12/1992 | European Pat. Off. . |
| WO9303067 | 2/1993 | WIPO . |
| WO9422926 | 10/1994 | WIPO . |

OTHER PUBLICATIONS

B. Rieger et al., *A Convenient Synthesis of Enantiomerically Pure Ethylene-Bridged Metallocene Complexes Bearing Fluorenyl- and Octahydrofluorenyl Ligands*[1] Chem. Ber. 1994, 127, 2417-2419.

Mejer et al., *Reduction With Lithiunm in Ethylenediamine. Part IV, Extensive Reduction of Polycyclic Aromatic Hydorcarbons to Cycloolefins With Double Bonds at Ring Junction*, Polish Journal of Chemistry, 53, 2385 (1979).

Llinas et al., $(C_5Me_5)SiMe_3$ *as a mild and effective reagent for transfer of the $C_5Me_5$ring: an improved route to monopentamethylcyclopentadienyl trihalides of the group 4 elements*, Journal of Organometallic Chemistry, 340 (1988) 37-40.

Primary Examiner—Porfirio Nazario-Gonzalez
Attorney, Agent, or Firm—Linda Blair Meier

[57] ABSTRACT

Octahydrofluorenyl metal complexes, such as octahydrofluorenyltitanium trichloride, or ring substituted octahydrofluorenyl metal complexes wherein the metal is in the +2, +3 or +4 formal oxidation state are prepared by reduction of tetra- or hexa-hydrofluorenyl metal complexes. The reduction reaction may be carried out at ambient pressure and temperature in the presence of a catalyst. The process of the present invention permits preparation of octahydrofluorenyltitanium metal complexes from a series of high yield reactions starting with fluorene.

18 Claims, No Drawings

METHOD FOR PRODUCING OCTAHYDROFLUORENYL METAL COMPLEXES

BACKGROUND OF THE INVENTION

This invention relates to a process for preparing octahydrofluorenyl metal complexes.

Metallocene catalysts are known to be useful in preparing polymers having a syndiotactic stereostructure. For example, highly syndiotactic vinyl aromatic polymers and other prochiral olefins are known to be prepared by use of titanium complexes containing a single cyclopentadienyl or substituted cyclopentadienyl group and an activating cocatalyst including alkylalumoxanes, inert, noncoordinating ion forming compounds, Lewis acids and mixtures thereof. Disclosure, of such prior art processes are found in U.S. Pat. Nos. 5,045,517, 5,066,741, 5,206,197 and WO 93/03067 (equivalent to U.S. Ser. No. 07/740529, filed Aug. 5, 1991). The teachings of all of the foregoing patents and patent applications and publications are hereby incorporated by reference.

In the absence of chain transfer agents in the above cited processes, syndiotactic vinyl aromatic polymers of molecular weight greater than 500,000 and often greater than 600,000 are generally prepared. Such polymers are difficult to process efficiently without undesired decomposition due to high temperatures. Consequently, metallocene catalysts capable of being used to prepare syndiotactic vinyl aromatic polymers, having reduced molecular weight are desirable. Therefore, there exists a need in the art for a high yield process to prepare such metallocene catalysts.

SUMMARY OF THE INVENTION

The present invention provides a high yield process for preparing octahydrofluorenyl transition metal complexes. The resulting octahydrofluorenyl transition metal complexes are useful as metallocene catalysts to form polymers which tend to be highly stereoregular polymers. For example, the resulting complexes may be used as catalysts to form polyethylene and/or polyolefins, and are particularly useful in the preparation of monovinylidene aromatic polymers that are highly syndiotactic. Use of these catalysts and suitable cocatalysts for polymerization is described in U.S. Ser. No. 08/316,748, filed Oct. 3, 1994, now allowed, the teachings of which is herein incorporated by reference. In accordance with the teachings of this reference, polymers having a desired low molecular weight less than 500,000 may be prepared.

According to the present invention there is provided a process for preparing octahydrofluorenyl metal complexes corresponding to the formula:

wherein:

E is an octahydrofluorenyl group or an octahydrofluorenyl group substituted with from 1 to 15 hydrocarbyl groups, each such hydrocarbyl group having 1 to 10 carbon atoms;

n is 1 or 2;

M is titanium, zirconium or hafnium in the +2, +3 or +4 formal oxidation state;

X is independently in each occurrence an anionic ligand group having up to 40 atoms;

p is 0, 1,2 or 3, and n+p equals the formal oxidation state of M;

X' is an inert, neutral donor ligand; and q is 0, 1, or 2. The process comprises the step of contacting a fluorenyl metal complex with hydrogen gas, wherein the fluorenyl metal complex corresponds to the formula:

wherein A is a tetrahydrofluorenyl group, a tetrahydrofluorenyl group substituted with from 1 to 13 hydrocarbyl groups, a hexahydrofluorenyl group, or a hexahydrofluorenyl group substituted with from 1 to 15 hydrocarbyl groups, each such hydrocarbyl group having 1 to 10 carbon atoms. Whenever used herein, variables A, E, n, M, X, p, X' and q are as defined immediately above.

DETAILED DESCRIPTION OF THE INVENTION

The process of the present invention involves a catalytic hydrogenation reaction of a fluorenyl metal complex to form an octahydrofluorenyl metal complex. The process may be represented generally as follows:

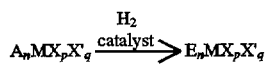

wherein the variables are as defined above. The fluorenyl metal complex (AnMXpX'q) may be contacted with the hydrogen by any method sufficient to form an octahydrofluoreqyl metal complex. This is typically accomplished by dissolving the fluorenyl metal complex (AnMXpX'q) in a suitable solvent, preferably in the presence of a catalytic amount of a hydrogenation catalyst, and introducing hydrogen gas into the fluorenyl metal complex solution. Each reaction described herein is conducted in a suitable noninterfering solvent at a temperature sufficiently high that reaction times are not inconveniently long, and typically below the boiling point of the solvent employed.

Hydrogen gas is generally introduced into a stirred fluorenyl metal complex solution at a sufficient pressure and for sufficient time to achieve hydrogenation of ligand A to ligand E. Completion of the above reaction is typically indicated by a change in the color of the solution. The reaction time for the hydrogenation step varies depending upon such factors as reactants used, reaction temperature, desired conversion level, agitation, excess organic compound, and reactor pressure. The skilled artisan is capable of determining the sufficient time required for reaction of hydrogen with the fluorenyl metal compound. Typically, sufficient reaction is achieved in less than 20 hours. The resulting product may be decanted and stripped of solvent by methods within the skill in the art.

The catalyst employed may be any catalyst capable of initiating hydrogenation. Illustrative but nonlimiting hydrogenation catalysts include platinum oxide (PtO2), platinum (Pt), palladium (Pd), Rhodium (Rh), Pd/Al$_2$O$_3$, and Rh/Al$_2$O$_3$. Preferably, the hydrogenation catalyst includes platinum, platinum oxide or palladium. The most preferred catalyst is platinum oxide. Catalyst may be added in any amount sufficient to induce reaction. The catalyst is typically added in an amount of about 1 to 10 weight percent based on the fluorenyl metal complex; preferably, about 4 weight percent.

B. Rieger and G. Jany in *Chem. Ber.* 1994, 127, 2417–2419 describe catalytic hydrogenation of bisfluorenyl complexes in a high pressure autoclave by filling the autoclave with H₂ at 200 bar (2900 psig or 20,000 kPa) and stirring the suspension for two days. The process of the present invention permits catalytic hydrogenation of fluorenyl complexes at significantly lower pressures. This provides an advantage of being able to perform the reaction in a less expensive reaction vessel. The maximum pressure under which the reaction takes place is typically less than about 800 psig (5500 kPa), preferably less than about 500 psig (3400 kPa), more preferably less than about 200 psig (1400 kPa), more preferably less than about 100 psig (690 kPa), more preferably less than about 50 psig (340 kPa), even more preferably less than about 30 psig (210 kPa), and most preferably less than about 20 psig (140 kPa). The minimum pressure under which the reaction takes place is limited by requiring the presence of hydrogen gas. The pressure in the head space of the reaction vessel is preferably greater than about 2 psig (14 kPa), more preferably greater than about 5 psig (34 kPa), and most preferably about ambient pressure (about 15 psig; 103 kPa).

The reaction temperature for the above hydrogenation reaction is typically lower than the boiling point of the solvent at the pressure at which the reaction is carried out. The reaction temperature is preferably less than about 40° C., more preferably less than about 30° C., and even more preferably less than about 25° C. The temperature is preferably greater than about 0° C., more preferably greater than about 15° C., even more preferably greater than about 20° C. because lower temperatures generally require cooling. Most preferably, the temperature is about ambient temperature (about 23°–25° C.).

Suitable reaction media for the formation of the metal complexes depend on the identity of the X ligands because the metal complex should be soluble in the reaction medium. Illustrative reaction media include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene; $C_{1-4}$ dialkyl ethers, $C_{1-4}$ dialkyl ether derivatives of (poly) alkylene glycols, and tetrahydrofuran, and mixtures thereof; and chlorinated aliphatics, particularly, methylene chloride, chloroform, tetrachloroethane and mixtures thereof. When X is halide, preferred solvents include halogenated aliphatics; more preferred solvents include chlorinated aliphatics; most preferred solvents include methylene chloride.

The above general definition and the following preferences apply in all the formulas described herein in which the variables are used, unless otherwise indicated. X is typically an anionic ligand exclusive of the class of ligands that are cyclic, delocalized N-bound ligand groups. Preferably, X is selected from the group consisting of halide, hydrocarbyl, hydrocarbyloxy, di(hydrocarbyl)amido, di(hydrocarbyl) phosphido, hydrocarbylsulfido, and silyl groups, as well as halo-, di(hydrocarbyl)-amino, hydrocarbyloxy- and di(hydrocarbyl)phosphino-substituted derivatives thereof, said X group having up to 20 nonhydrogen atoms. More preferably, X is halide, or $C_{1-4}$ linear alkoxide or phenoxide. Even more preferably, X is halide; most preferably, X is chloride.

Illustrative but nonlimiting examples of X' include ROR, RSR, NR₃, PR₃, and $C_{2-20}$ olefins or diolefins, wherein R is $C_{1-20}$ hydrocarbyl. Such donor ligands are able to form shared electron bonds but not a formal covalent bond with the metal. Typically, q is 0 or 1; preferably q is 0 such that the complex has no X' ligand.

A is preferably a tetrahydrofluorenyl group or a tetrahydrofluorenyl group substituted with from 1 to 13 hydrocarbyl groups. Most preferably, A is an unsubstituted tetrahydrofluorenyl group. Preferably, n is 1. Correspondingly, E is preferably an octahydrofluorenyl group or an octahydrofluorenyl group substituted with from 1 to 13 hydrocarbyl groups, each such hydrocarbyl group having 1 to 10 carbon atoms; most preferably E is an unsubstituted octahydrofluorenyl group.

M is preferably titanium or zirconium. More preferably, M is titanium; most preferably, M is titanium in the +4 oxidation state.

Preferred fluorenyl metal complexes (AnMXpX'q) correspond to the formula:

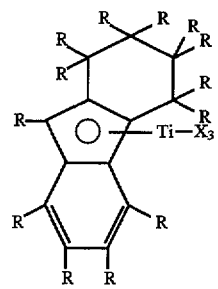

wherein:

R is independently in each occurrence hydrogen or $C_{1-10}$ alkyl; and

X is as defined above. Preferably, R is hydrogen in each occurrence such that A is an unsubstituted tetrahydrofluorenyl group. Thus, in a highly preferred embodiment, A is a tetrahydrofluorenyl group, M is titanium, n is 1, q is 0, and p is 3. Most preferably, X is chloride.

Examples of octahydrofluorenyl metal complexes which may be prepared by the above hydrogenation reaction include: octahydrofluorenyltitanium (IV) trichloride; octahydrofluorenyltitanium (IV) trimethoxide; octahydrofluorenyltitanium (IV) triphenoxide; octahydrofluorenyltitanium (IV) dichloride phenoxide; octahydrofluorenyltitanium (III) dimethoxide; and octahydrofluorenyltitanium (III) methyl (2-dimethylaminobenzyl). Additional complexes which may be prepared as described herein will be readily apparent to the skilled artisan.

Highly preferred octahydrofluorenyl metal complexes are octahydrofluorenyltitanium (IV) trichloride, and octahydrofluorenyltitanium (IV) trimethoxide.

If the X groups are halide in the resulting octahydrofluorenyl metal complex ($E_nMX_pX'_q$), then the octahydrofluorenyl metal complex may be further reacted to form an octahydrofluorenyl alkoxide complex by contacting the octahydrofluorenyl metal complex (wherein X is halide) with an alkali metal alkoxide compound.

The octahydrofluorenyl metal complex may be contacted with the alkali metal alkoxide compound by any method sufficient to form an octahydrofluorenyl alkoxide. This is typically accomplished by dissolving the octahydrofluorenyl metal complex ($E_nMX_pX'_q$) in a suitable solvent, cooling the solution, adding the alkali metal alkoxide to the solution, and stirring the mixture until the reaction is complete.

For availability, the alkali metal alkoxide compound preferably has from 1 to 10 carbon atoms, and is preferably sodium alkoxide. Illustrative alkali metal alkoxide compounds include potassium t-butoxide, sodium methoxide, sodium ethoxide and sodium phenoxide. Most preferably the compound is sodium methoxide. The halide X group is thereby substituted with the alkoxy group of the alkali metal alkoxide. This and each reaction described below is preferably carried out under an inert atmosphere such as a nitrogen or argon atmosphere.

This reaction is preferably carried out and in an aromatic hydrocarbon or ether-type solvent. Examples of suitable solvents are listed above. More preferably, the solvent is an aromatic hydrocarbon; most preferably, the solvent is toluene.

The reaction temperature is not critical. The temperature is preferably in the range of about 0° C. to about room temperature (about 23°–25° C.).

The number of equivalents of alkali metal alkoxide is preferably in slight excess of the value of p (the number of X ligands). For example, for the complex octahydrofluorenyltitanium (IV) trichloride, p is 3. Therefore, alkali metal alkoxide would preferably be added in an amount in excess of 3 molar equivalents of alkoxide to one molar equivalent of octahydrofluorenyltitanium (IV) trichloride if full substitution of the halide X ligands for an alkoxy groups is desired. If full substitution is not desired, the molar ratio may be adjusted accordingly as is readily apparent to the skilled artisan.

Returning to the original hydrogenation process described above, the fluorenyl metal complex (AnMXpX'q) which is used as a reactant in the process may be produced by contacting a silyl fluorene compound with a transition metal halide. The silyl fluorene compound corresponds to the formula:

AY wherein:

A is as defined above, including the preferences;

Y is an alkali metal or $SiZ_3$ wherein:

Si is silicon; and

Z is a hydrocarbyl group having up to 6 carbon atoms.

This reaction may be represented generally as follows:

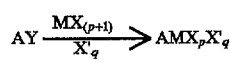

wherein, as defined above,

M is titanium, zirconium or hafnium in the +2, +3 or +4 formal oxidation state;

X is an anionic ligand group having up to 40 atoms exclusive of the class of ligands that are cyclic, delocalized, II-bound ligand groups;

p is 1, 2 or 3, and n+p equals the formal oxidation state of M;

X' is an inert, neutral donor ligand; and q is 0, 1, or 2. $MX_{(p+1)}$ represents a transition metal halide. The preferences indicated above for these variables also apply here. Y is typically a silyl group ($SiZ_3$) or an alkali metal such as lithium, sodium, potassium, rubidium or cesium. Y is preferably lithium or a silyl group; more preferably, a silyl group ($SiZ_3$). Z is typically a methyl, ethyl, propyl, butyl, or phenyl group; preferably methyl. The X' group may come from the solvent or from an additive to the solvent.

Any operable process conditions may be employed provided that a fluorenyl metal complex is produced. This is typically accomplished by dissolving the fluorenyl metal complex and the transition metal halide, and mixing the dissolved reactants for a sufficient time to achieve the desired reaction.

Illustrative solvents for this reaction include straight and branched chain hydrocarbons, such as methane, ethane, propane, butane, isobutane, pentane, hexane, heptane, and octane; chlorinated hydrocarbons, aromatic hydrocarbons; and ether-type hydrocarbons as defined above, and mixtures thereof. Preferably, the solvent is a chlorinated hydrocarbon when Y is $SiZ_3$.

Conditions of temperature, pressure and reaction time are not critical. Typically, the process temperature falls between about 0° C. and 70° C., preferably between about 15° C. and 30° C. Below the lower typical temperature the conversion may be low or reaction times long. Above the typical upper temperature the conversion the solvent may boil. The pressure is preferably about ambient pressure. At ambient pressure and temperature, the reaction is typically complete in less than about 20 hours.

The relative amounts of the reactants can vary within any operable range provided that the predominant product is a fluorenyl metal complex. Typically, the molar ratio of silyl fluorene compound ($ASiZ_3$) to transition metal halide ($MX_{(p+1)}$) is from about 10:1 to about 1:10; preferably, from about 4:1 to about 1:4; most preferably, the molar ratio is about 1:1.

The transition metal halide ($MX_{(p+1)}$) is preferably selected from the group consisting of $TiCl_4$, $TiBr_4$, $TiI_4$, $ZrCl_4$, and $HfCl_4$. More preferably, the transition metal halide is $TiCl_4$, $TiBr_4$, or $TiI_4$; preferably, $TiCl_4$.

Illustrative alkali metal fluorene compounds (A-Y wherein Y is an alkali metal) include hexahydrofluorenyl lithium or tetrahydrofluorenyl lithium, hexahydrofluorenyl potassium or tetrahydrofluorenyl potassium, and the corresponding sodium, rubidium and cesium compounds. Lithium compounds are preferred.

Illustrative silyl fluorene compounds (AY wherein Y is $SiZ_3$) include trimethylsilyl hexahydrofluorene, trimethylsilyl tetrahydrofluorene, triethylsilyl hexahydrofluorene, triethylsilyl tetrahydrofluorene, tributylsilyl hexahydrofluorene, tributylsilyl tetrahydrofluorene, etc. Preferably, the silyl fluorene compound ($ASiZ_3$) is trimethylsilyl tetrahydrofluorene.

The silyl fluorene compound ($ASiZ_3$) used in the above process may be produced by the following two-step reaction. The first step is to contact an alkyllithium compound with tetrahydrofluorene substituted with from 0 to 13 hydrocarbyl groups or hexahydrofluorene substituted with from 0 to 15 hydrocarbyl groups. This first step results in an alkali metal fluorene compound AY wherein Y is lithium. The second step is to contact the product of step one with a silyl halide compound corresponding to the formula $DSiZ_3$ wherein D is a halide and Z is a hydrocarbyl group having up to 6 carbon atoms, as defined above. This two-step reaction may be represented generally as follows:

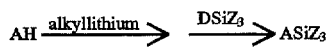

wherein H is a hydrogen atom; Si is silicon; D is halide; and Z and A are as defined above, including the preferences indicated. Preferably, D is chloride. Preferably, Z is a methyl group. Most preferably, the silyl halide ($DSiZ_3$) is trimethylsilyl chloride.

The of substituted or unsubstituted tetra- or hexa-hydrofluorene may be contacted with the alkylllithium compound and that product contacted with a silyl halide compound by any methods sufficient to form a silyl fluorene compound ($ASiZ_3$). The first step of this reaction is typically carried out by cooling a solution of substituted or unsubstituted tetra- or hexa-hydrofluorene and slowly adding a solution of alkyllithium compound. The second step of this reaction is typically carried out by cooling the solution from step one and slowly adding a silyl halide compound. The reaction time is not critical for either step. The alkyllithium compound is typically added over a period of several minutes. After complete addition, completion of reaction may be indicated by precipitation of lithium salt from the solution which is generally within a few minutes. The silyl halide compound is typically added over a period of about one hour and the solution stirred for several hours after complete addition. Reaction is typically complete within about 12 hours.

Preferred solvents include ether-type solvents such as $C_{1-4}$ dialkyl ethers, $C_{1-4}$ dialkyl ether derivatives of (poly) alkylene glycols, and tetrahydrofuran, and mixtures thereof. Most preferably, the solvent is THF.

The pressure is not critical and is conveniently about ambient pressure. The reaction is preferably carried out in an inert atmosphere such as a nitrogen atmosphere or an argon atmosphere.

The first step is preferably carried out at a temperature of about −78° C. to 0° C.; most preferably about −10° C. The second step is preferably carried out at a temperature of about −78° C. to 0° C.; most preferably about −15° C.

Preferred alkyllithium compounds are those having from 1 to 6 carbon atoms. Illustrative alkyllithium compounds include methyllithium, ethyllithium, propyllithium, butyllithium, pentyllithium, hexyllithium, and phenyllithium. The alkyllithium compound is preferably butyllithium, or methyllithium; most preferably n- butyllithium. Typically, the molar ratio of alkyllithium compound to substituted or unsubstituted tetra- or hexa-hydrofluorene is from about 10:1 to about 1:2; preferably, the molar ratio is about 1:1. Similarly, the molar ratio of silyl halide to substituted or unsubstituted tetra- or hexa-hydrofluorene is typically about the same as the molar ratio used of alkyllithium compound to substituted or unsubstituted tetra- or hexa-hydrofluorene; preferably, both molar ratios are about 1:1. The silyl halide and the alkyllithium compound are generally added in slight excess.

Tetrahydrofluorene which is substituted with from 0 to 9 hydrocarbyl groups may be produced by the step of contacting fluorene or fluorene substituted with 1 to 9 hydrocarbyl groups with at least about 4 equivalents of lithium metal. The contacting may be done in any reaction conditions sufficient to provide the desired reduction. The reaction is typically accomplished by dissolving the substituted or unsubstituted fluorene in a suitable solvent, cooling the fluorene solution, and slowly adding lithium metal to the solution.

The lithium metal is typically added in small portions introduced a few minutes apart in order to maintain a relatively low temperature. The reaction time is not critical, and is typically complete within a few hours of complete addition of the lithium metal. The pressure under which the reaction takes place is not critical. The reaction is preferably carried out under an inert atmosphere such as nitrogen or argon. After reaction, the product may be recovered by any technique known in the art. Preferably the resulting tetrahydrofluorene is recovered by extraction with aqueous and organic solutions, followed by phase separation and stripping of the organic solvent. The starting material is preferably unsubstituted fluorene; therefore, this reaction provides a first step to producing octahydrofluorenyl metal complexes from fluorene.

This reduction reaction may be carried out generally as in S. Mejer, et al., Pol. J. Chem. 53 (1979) 2385, the teachings of which are herein incorporated by reference.

The temperature is typically from about −10° to 25° C.; preferably, from about 0° C. to about room temperature (25° C.); most preferably from about 0° C. to about 10° C. before addition of lithium because the reaction is exothermic.

Temperature control may be achieved by any means within the skill of the art, such as an ice bath.

The number of equivalents of lithium metal for each one equivalent of fluorene or substituted fluorene is typically greater than about 4 in order to provide reduction of one of the six membered rings on the fluoreric molecule. Preferably, the number of equivalents of lithium metal is less than about 8, and more preferably less than about 5.

The solvent may be any solvent described above. Preferably the solvent is a mixture of ethylene diamine and an ether-type solvent, such as THF or diethyl ether. More preferably, the solvent is a mixture of ethylenediamine and THF; most preferably this mixture is 1:1 by volume.

The skilled artisan will appreciate that the invention disclosed herein may be practiced in the absence of any component which has not been specifically disclosed. The following examples are provided as further illustration thereof and are not to be construed as limiting. Unless stated to the contrary all parts and percentages are expressed on a weight basis. All products in the examples below were identified by $^1$H NMR spectroscopy.

EXAMPLES

The following examples describe a series of high yield reactions to produce octahydrofluorenyl titanium trichloride and octahydrofluorenyl titanium trimethoxide from fluorene.

1,2,3,4-tetrahydrofluorene.

Fluorene (100 g, 0.6 mole) was dissolved in a mixture of 600 ml tetrahydrofuran (THF) and 600 ml ethylenediamine (1:1 by volume). The fluorene solution was degassed with nitrogen and cooled to 0° C. 4.25 equivalents of lithium metal (17.7 g, 2.55 mole) were added in 2 g portions every 10 minutes and the reaction temperature was maintained at 10° C. The reaction mixture was warmed to room temperature. The reaction mixture was then quenched with degassed water; the separated organic phase was extracted with a mixture of aqueous NaCl (300 ml) and cyclohexane (500 ml). The organic phase was washed with aqueous NaCl (300 ml), the water phase was removed, and the cyclohexane was stripped from the solution leaving 95 g (0.56 moles) of tetrahydrofluorene (93% yield). 9-trimethylsilyl-1,2,3,4-tetrahydro-9H-fluorene. 1,2,3,4-tetrahydro-9H-fluorene (50 grams (g), 0.294 mol) was dissolved in 1 liter (L) of anhydrous THF and cooled to −78 ° C. To this solution 123 ml (0.307 mol) of n-BuLi (2.5M solution in hexane) was added via syringe within 25 minutes (min). The reaction mixture was stirred for few minutes at −78° C. until the lithium salt precipitated from the solution. After precipitation, the cold bath was removed and the reaction mixture was and stirred for 2 hours (hr) at room temperature. The flask was cooled to −78° C. and 40 ml (34.24 g, 0.315 mol) of trimethylsilyl chloride (TMSCI) was added through syringe within 1 hr. After addition was completed the reaction mixture was stirred for 3 hr at −78 ° C. and then it was slowly warmed up to room temperature and stirred overnight. THF solvent was removed in vacuum and the residue was extracted with 150 ml of hexane. The hexane solution was filtered to another flask and hexane was removed leaving 70.39 g of 9-trimethylsilyl-1,2,3,4-tetrahydro-9H-fluorene (about 95% pure). Yield 99%.

($\eta^5$-tetrahydrofluorenyl)titanium trichloride. To a 1L flask containing 65.78 g (0.2713 mol) of 9-trimethylsilyl-1,2,3, 4-tetrahydro-9H-fluorene in 500 ml of anhydrous $CH_2Cl_2$ was added 29.8 ml (51.474 g, 0.2713 mol) of $TiCl_4$ through syringe within 1 minute. The color of the reaction mixture became black within few minutes. The reaction mixture was stirred overnight (about 20 hr). The solvent was removed in vacuum and the residue was washed with 200 ml of hexane. The residue was dried in vacuum for 1 hr leaving 75.18 g (0.232 mol) of pure product. Yield 85.6%.

($\eta^5$-octahydrofluorenyl)titanium trichloride. ($\eta^5$-tetrahydro-fluorenyl)titanium trichloride (75.18 g, 0.232 mol) and 3 g of $PtO_2$ was dissolved in 900 ml of anhydrous $CH_2Cl_2$ in a 3L flask. The flask was cooled to $-78°$ C. and then a vacuum was applied to remove the nitrogen from the solution. The flask was subsequently pressurized with 15 psi of hydrogen gas and the reaction mixture was stirred overnight (18 hr.) resulting in a red-orange reaction mixture. Stirring was stopped for 1 hr. during which the $PtO_2$ settled. The upper portion of the solution (about 90%) was transferred to another flask. The remaining solution with $PtO_2$ was diluted with 150 ml of $CH_2Cl_2$ and the upper portion of the solution was transferred and combined with the first collected solution. This operation was repeated once. The $CH_2Cl_2$ was removed in vacuum leaving 73 g of ($\eta^5$-octahydrofluorenyl)titanium trichloride. Yield 97%.

($\eta^5$-octahydrofluorenyl)titanium trimethoxide.

Octahydrofluorenyltitanium trichloride (51 g, 0.156 mol) was dissolved in 500 ml anhydrous toluene and the solution was cooled to $0°$ C. Sodium methoxide (26.8 g, 0.49 mol) was added and the reaction mixture stirred overnight at room temperature. The product was washed with 200 ml hexane and NaCl was filtered. The hexane was removed leaving 44 g (0.14 mol) ($\eta^5$-octahydrofluorenyl)titanium trimethoxide. Yield 90%.

What is claimed is:

1. A process for producing octahydrofluorenyl metal complexes corresponding to the formula:

$$E_nMX_pX'_q$$

wherein:

E is an octahydrofluorenyl group or an octahydrofluorenyl group substituted with from 1 to 15 hydrocarbyl groups, each such hydrocarbyl group having 1 to 10 carbon atoms;

n is 1 or 2;

M is titanium, zirconium or hafnium in the +2, +3 or +4 formal oxidation state;

X is independently in each occurrence an anionic ligand group having up to 40 atoms;

p is 0, 1, 2 or 3, and n+p equals the formal oxidation state of M;

X' is an inert, neutral donor ligand; and q is 0, 1, or 2;

the process comprising the step of contacting a fluorenyl metal complex with hydrogen gas, the fluorenyl metal complex corresponding to the formula:

$$A_nMX_pX'_q$$

wherein A is a tetrahydrofluorenyl group, a tetrahydrofluorenyl group substituted with from 1 to 13 hydrocarbyl groups, a hexahydrofluorenyl group, or a hexahydrofluorenyl group substituted with from 1 to 15 hydrocarbyl groups, each such hydrocarbyl group having 1 to 10 carbon atoms.

2. The process of claim 1 wherein the reaction pressure is less than about 800 psi (5500 kPa).

3. The process of claim 2 wherein the reaction pressure is between about 2 psi (14 kPa) and 50 psig (340 kPa).

4. The process of claim 1 wherein q is 0.

5. The process of claim 1 wherein n is 1.

6. The process of claim 1 wherein M is titanium.

7. The process of claim 1 wherein X is exclusive of the class of ligands that are cyclic, delocalized, Π-bound ligand groups.

8. The process of claim 1 wherein the fluorenyl metal complex corresponds to the formula:

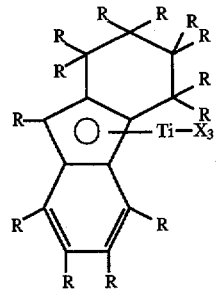

wherein:

R is independently in each occurrence hydrogen or $C_{1-10}$ alkyl; and

X is independently in each occurrence an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms.

9. The process of claim 8 wherein X is chloride, $C_{1-4}$ linear alkoxide, or phenoxide.

10. The process of claim 1 wherein the octahydrofluorenyl metal complex is octahydrofluorenyltitanium trichloride or octahydrofluorenyltitanium trimethoxide.

11. The process of claim 1 wherein the fluorenyl metal complex is produced by the step of contacting a silyl fluoreric compound with a transition metal halide; the silyl fluoreric compound corresponding to the formula:

$$ASiZ_3$$

wherein:

A is as defined in claim 1;

Si is silicon; and

Z is a hydrocarbyl group having up to 6 carbon atoms.

12. The process of claim 11 wherein the transition metal halide is selected from the group consisting of $TiCl_4$, $TiBr_4$, $TiI_4$, $ZrCl_4$, and $HfCl_4$.

13. The process of claim 11 wherein the silyl fluorene compound is trimethyl silyl tetrahydrofluorene.

14. The process of claim 11 wherein the silyl fluorene compound is produced by the steps of:

(i) contacting an alkyllithium compound with tetrahydrofluorene substituted with from 0 to 13 hydrocarbyl groups or hexahydrofluorene substituted with from 0 to 15 hydrocarbyl groups; and (ii) contacting the product of step (i) with a silyl halide compound corresponding to the formula $DSiZ_3$ wherein D is a halide and Z is as defined in claim 10.

15. The process of claim 14 wherein D is chloride.

16. The process of claim 14 wherein Z is a methyl group.

17. The process of claim 14 wherein the tetrahydrofluorene is substituted with from 0 to 9 hydrocarbyl groups and is produced by the step of:

contacting fluorene or fluorene substituted with 1 to 9 hydrocarbyl groups with at least about 4 equivalents of lithium metal.

18. The process of claim 1 further comprising the step of contacting the octahydrofluorenyl metal complex, wherein X is halide, with an alkali metal alkoxide compound to form an octahydrofluorenyl alkoxide complex.

* * * * *

UNITED STATES PATENT AND TRADEMARK OFFICE
CERTIFICATE OF CORRECTION

PATENT NO. : 5,670,680
DATED : September 23, 1997
INVENTOR(S) : Thomas H. Newman et al.

It is certified that error appears in the above-identified patent and that said Letters Patent is hereby corrected as shown below:

Claim 11, column 10, line 42, "fluoreric" should read -- flourene--.

Claim 11, column 10, line 43, "fluoreric" should read -- flourene--.

Signed and Sealed this

Nineteenth Day of September, 2000

Attest:

Q. TODD DICKINSON

*Attesting Officer*   *Director of Patents and Trademarks*